United States Patent [19]
Saito et al.

[11] Patent Number: 5,288,563
[45] Date of Patent: Feb. 22, 1994

[54] HYDROGEN ION CONCENTRATION SENSOR AND LEAD-ACID BATTERY HAVING THE SENSOR

[75] Inventors: Satoshi Saito; Yuko Fujita, both of Kyoto, Japan

[73] Assignee: Japan Storage Battery Co., Ltd., Kyoto, Japan

[21] Appl. No.: 835,391

[22] Filed: Feb. 14, 1992

[30] Foreign Application Priority Data

| | | | |
|---|---|---|---|
| Feb. 18, 1991 | [JP] | Japan | 3-046057 |
| Jul. 19, 1991 | [JP] | Japan | 3-204707 |
| Jul. 19, 1991 | [JP] | Japan | 3-204708 |

[51] Int. Cl.$^5$ .................................................. H01M 2/00
[52] U.S. Cl. .................................................. 429/91; 429/90
[58] Field of Search .................................... 429/90, 91

[56] References Cited

U.S. PATENT DOCUMENTS

| | | | |
|---|---|---|---|
| 4,409,980 | 10/1983 | Yano et al. | 128/635 |
| 4,791,465 | 12/1988 | Sakai et al. | 357/25 |

FOREIGN PATENT DOCUMENTS

| | | |
|---|---|---|
| 2254207 | 11/1973 | Fed. Rep. of Germany . |
| 60-62066 | 4/1985 | Japan . |
| 60-112266 | 6/1985 | Japan . |

OTHER PUBLICATIONS

Preprint for the 34th Meeting of Anl. Chem Soc. Jap., 2D05, p. 489, 1985 Kodaiku, et al.
D. Ammann et al., Anal. Chem., 53, 2267, 1981 "Neutral Carrier Based Hydrogen Ion Selective Microelectrode".
Matsuo et al., Denki Kagaku, 50 (1) (1981) pp. 64–71.
Wakida et al., Preprint for the 58th Spring Meeting of Chem. Soc. Jap., 1,31G17, p. 360, 1989.
J. L. Weininger et al., J. Electrochem. Soc., 129, 2409, 1982 "State–of–Charge Indicator for Lead–Acid Batteries".
Matsuo et al., Oyo Butsuri, 49, 586, 1980 "Field Effect Transistor Type Chemical Sensor".

*Primary Examiner*—Olik Chaudhuri
*Assistant Examiner*—C. Everhart
*Attorney, Agent, or Firm*—Sughrue, Mion, Zinn, Macpeak & Seas

[57] ABSTRACT

A device for measuring hydrogen ion concentration in an aqueous solution includes a sensing means for sensing hydrogen ion concentration and a reference electrode. The sensing means may be an ion-sensitive field-effect transistor or a hydrogen ion electrode. The sensing means has an ion-sensitive layer composed of tantalum nitride, niobium nitride, zirconium nitride or niobium oxide. When the sensing device is built integrally into a lead-acid battery, the state of charge-discharge of the battery can be effectively known.

20 Claims, 2 Drawing Sheets

HYDROGEN ION CONCENTRATION SENSOR AND LEAD-ACID BATTERY HAVING THE SENSOR

This invention relates to a device for measuring the concentration of hydrogen ions in an aqueous solution, as well as a lead-acid battery equipped with the device.

BACKGROUND OF THE INVENTION

Hydrogen ion electrodes used for measuring the concentration of hydrogen ions in aqueous solutions and pH meters using a glass electrode are widely known. A "solid membrane-type" hydrogen ion electrode has also been proposed in which an ion sensing material such as dodecamolybdophosphoric acid (Kodaiku, Murata and Ikeda, *Preprint for the 34th Meeting of Anal. Chem. Soc. Jap.*, 2D05, p. 489, 1985) or dodecylamine (D. Ammann et al., *Anal. Chem.*, 53, 2267, 1981) is immobilized with a suitable material such as a polymer. There have also been proposed ion-selective field-effect transistors (ISFET) that use an oxide (e.g., $SiO_2$, $Al_2O_3$ or $Ta_2O_5$), $Si_3N_4$ (Matsuo and Esashi, Denki Kagaku, 50, 64, 1982), or titanium nitride (TiN) (Wakida, Makabe, Mochizuki, Yamane and Higashi, *Preprint for the 58th Spring Meeting of Chem. Soc. Jap.*, 1,3IG17, p. 360, 1989) as a hydrogen ion sensing material.

In lead-acid batteries, the charge-discharge reaction takes place according to the following scheme:

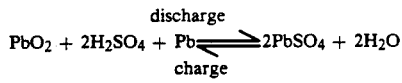

$$PbO_2 + 2H_2SO_4 + Pb \underset{\text{charge}}{\overset{\text{discharge}}{\rightleftharpoons}} 2PbSO_4 + 2H_2O$$

As the discharge proceeds in the battery, sulfuric acid ($H_2SO_4$) as the electrolyte is consumed and its concentration decreases. Conversely, if the charge proceeds, sulfuric acid is produced and its concentration increases. Thus, the consumption or production of sulfuric acid in the lead-acid battery is proportional to the amount of discharge or charge (ampere-hour), and thus a specific stage of the transition from a charged to a discharged state or vice versa, or residual capacity of the battery can be determined by measuring the sulfuric acid concentration.

A float-type hydrometer and a light refraction-type hydrometer are commercially used today to determine a specific stage of the transition from a charged to a discharged state or vice versa of lead-acid batteries using the principle described above. However, these hydrometers are generally bulky and are not used as an integral part of the lead-acid battery. Instead, part of the electrolyte is pumped out of the battery so that the specific gravity of the electrolyte can be measured with the hydrometers. Therefore, those hydrometers are not applicable to sealed lead-acid batteries.

To enable measuring the electrolyte concentration in sealed lead-acid batteries, various methods have been proposed. One method determines the concentration of an aqueous sulfuric acid solution by measuring humidity with a humidity sensor relying on the vapor pressure in the space above the sulfuric acid solution which is in gas-liquid equilibrium with the solution being dependent on its concentration, as described in West German Patent No. 2,254,207. This method has been refined such that the partial pressure of water vapor diffusing through pores in a porous polypropylene membrane which envelops a humidity sensor is measured with the sensor (J. L. Weininger et al., *J. Electrochem. Soc.*, 129, 2409, 1982). Another method uses an electrode-type hydrometer that operates on the principle that the potential difference between a lead dioxide electrode and a lead electrode depends on the concentration of sulfuric acid (see, for example, Japanese Patent Unexamined Publication No. Sho. 60-62066).

Hydrogen ion electrodes typified by pH meters have heretofore been inapplicable in strong acidic or alkaline aqueous solutions since the linearity based on the Nernst equation generally cannot be obtained outside the so-called "pH measuring range" (pH 2-12), and this phenomenon is commonly referred to as "acid error" or "alkali error". The concentration of the aqueous sulfuric acid solution used in lead-acid batteries is generally within the range of ca. 5.2–0.8 mol/L (ca. 1.28–1.05 in terms of specific gravity), so there has been no reported attempt of using a hydrogen ion electrode as a sensor for measuring sulfuric acid concentration in lead-acid batteries.

The only exception is the solid membrane-type hydrogen ion sensor that has dodecamolybdophosphoric acid fixed with a binder (Kodaiku et al., *Preprint for the 34th Meeting of Anal. Chem. Soc. Jap.*, ibid.). Although the report asserts that the operation of the sensor complies with the Nernst equation over the working concentration range of the aqueous sulfuric acid solution used in the lead-acid battery, this method is still in the development stage and lacks reliability.

A method of using an ion-selective field-effect transistor (ISFET) in a device for sensing the specific gravity of lead-acid batteries has already been made public (Japanese Patent Unexamined Publication No. Sho. 60-12266), but there is no disclosure as to what material the ion sensing layer in the ISFET contains. Tantalum oxide ($Ta_2O_5$) has been reported to exhibit the best characteristics as the oxide and nitride coatings provided on the field-effect transistor to measure the hydrogen ion concentration (Matsuo and Esashi, *Oyo Butsuri*, 49, 586, 1980). However, the ISFET using $Ta_2O_5$ is disadvantageous in that if the ISFET is submerged in sulfuric acid having a concentration commonly used for the electrolyte in lead-acid batteries, the potential of the sensor will become unstable in a few months.

Further, the method of measuring the sulfuric acid concentration with the conventional humidity sensor is generally slow in its response, and has the added disadvantage that the vapor of sulfuric acid will corrode the sensor. The electrode-type hydrometer described in Japanese Patent Unexamined Publication No. Sho. 60-62066 suffers from a serious operational disadvantage in that to compensate the self-discharge of the electrode, an electric current must occasionally be supplied from an external circuit to conduct electrochemical oxidation and reduction.

Sealed lead-acid batteries present another problem that is peculiar to their structure. Generally, a very small amount of an aqueous solution of sulfuric acid is retained in the glass mat which serves not only as a separator, but also as an electrolyte retainer. Thus, the presence of a free electrolyte is negligible. Hence, a device for sensing hydrogen ion concentration must be used which is compact enough to measure the concentration of sulfuric acid present in the glass mat.

SUMMARY OF THE INVENTION

The present invention has been designed in view of the above-described problems of the conventional systems, and has an object of providing a hydrogen ion concentration sensor having a reference electrode combined with a hydrogen ion electrode, and which has the surface of a gate insulator layer in an FET or a metal surface coated with an ion sensing material selected from among tantalum nitride, niobium nitride, zirconium nitride and niobium oxide.

The present invention also provides a lead-acid battery in which the above-described sensing device is built thereinto to detect the concentration of the sulfuric acid used as the electrolyte, thereby monitoring a specific transition stage from a charged to a discharged state or vice versa of the lead-acid battery.

DETAILED DESCRIPTION OF THE PREFERRED EMBODIMENT

Figure 1:
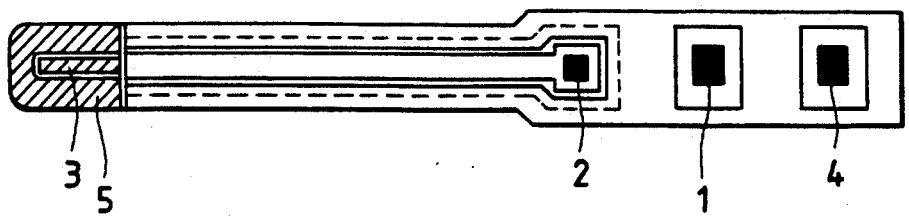
FIG. 1 is a cross-sectional view showing the construction of an ion-selective FET fabricated according to the present invention, having a source 1, a drain 2, a gate 3, a diode 4, and an ion sensing layer 5 formed on the gate 3.

The present inventors fabricated a hydrogen ion sensing device in which the surface of the gate insulator layer of an ISFET or a metallic surface was coated with tantalum nitride (TaN) as a hydrogen ion sensing material. This device showed a linear relationship between potential and the logarithm of the hydrogen ion activity at hydrogen ion concentrations ranging from $10^{-6}$ to 2 mol/L. The present inventors also found that the sensitivity of the device, or the change in potential in response to the 10-fold change in activity, was about 60 mV.

No details have yet been established for the mechanism of potential response of tantalum nitride to hydrogen ion. However, if an ion-selective FET or a hydrogen ion electrode that uses tantalum nitride as a hydrogen ion sensing material is submerged in an aqueous solution of interest that contains hydrogen ions, the following Nernst equation will hold for the relationship between potential E and the hydrogen ion activity ($a_{H^+}$) mol/L:

$$E = 2.303 \times (RT/F) \times \log[a_{H^+}].$$

Hence, the activity of hydrogen ions in the aqueous solution of interest can be determined by measuring the potential difference between the hydrogen ion electrode and a suitable reference electrode. Since the relationship between the hydrogen ion activity and concentration is known for various acid solutions, the concentration of a certain acid solution can be determined from the potential difference measurement on that solution. Additionally, the above-mentioned Nernst equation holds true with the ion-selective FET or the hydrogen ion electrode not only over the ordinary lower hydrogen ion concentration of $10^{-6}-2$ mol/L, but also over the higher range of 5.2–0.8 mol/L for the sulfuric acid used as electrolytes in lead-acid batteries. It was also found that the potential characteristics of the ISFET or the electrode would not change even when submerged in sulfuric acid of a high concentration for a period longer than half a year. The present invention has been accomplished based on these findings, and as mentioned above, it has been known in the art that the data obtained with the hydrogen ion electrode will generally deviate from the Nernst equation at high acid concentrations over the range normal to the sulfuric acid used as electrolytes in lead-acid batteries. Therefore, it should be understood that the above-described findings by the present inventors are extremely important in view of the common knowledge in the art hitherto the invention.

Besides enabling high sensitivity for hydrogen ion detection, tantalum nitride has another advantage in that it is not attacked by high concentrations of sulfuric acid, and thus the hydrogen ion electrode using tantalum nitride is suitable for use in lead-acid batteries.

The present inventors further found that besides tantalum nitride, other ion sensing materials such as niobium nitride, zirconium nitride and niobium oxide exhibited a similar response to the hydrogen ions.

The reference electrode to be used in the present invention may be a conventionally known Ag/AgCl electrode and it may be built integrally with an FET together with the hydrogen ion electrode used as a measuring electrode.

The above-described ISFET system has the particular advantage that it can be formed as a thin wire having a cross-sectional area as small as approximately 0.23×0.5 mm, so that it can be easily installed in lead-acid batteries, especially those of a sealed type which contain a very small amount of electrolyte. The significance of this advantage is well recognized if one considers that the cross-sectional diameter of a solid membrane-type hydrogen ion electrode having a dodecamolybdophosphoric acid immobilized with polyvinyl chloride can hardly be reduced to less than 10 mm.

The hydrogen ion electrode of the present invention is suitably installed in a space between either one of the electrodes in a lead-acid battery and the separator. However, this configuration is not the sole one envisioned for the present invention. The advantages of the present invention are particularly noticeable if the sensing device is applied to sealed lead-acid batteries, but needless to say the sensing device is also effective with non-sealed-type batteries.

The following examples are provided for the purpose of further illustrating the present invention, but are in no way to be taken as limiting the invention thereto.

EXAMPLE 1

A thin film of tantalum nitride (TaN) was formed on the gate insulator layer of an FET measuring 0.5×6.5×0.23 mm by a high-frequency magnetron sputtering method. Thereafter, the thus-formed thin film serves as an ion sensing layer. The sputtering apparatus was filled with a gaseous mixture of argon and nitrogen, with the nitrogen partial pressure being $1 \times 10^{-2}$ Pa. The thus formed thin tantalum nitride film had a thickness of ca. 4000 Å. The construction of the fabricated ion-selective FET, shown schematically in FIG. 1, includes a source 1, a drain 2, a gate 3, a diode 4, and the thin film of tantalum nitride (TaN) 5 formed on the gate 3.

Figure 2:
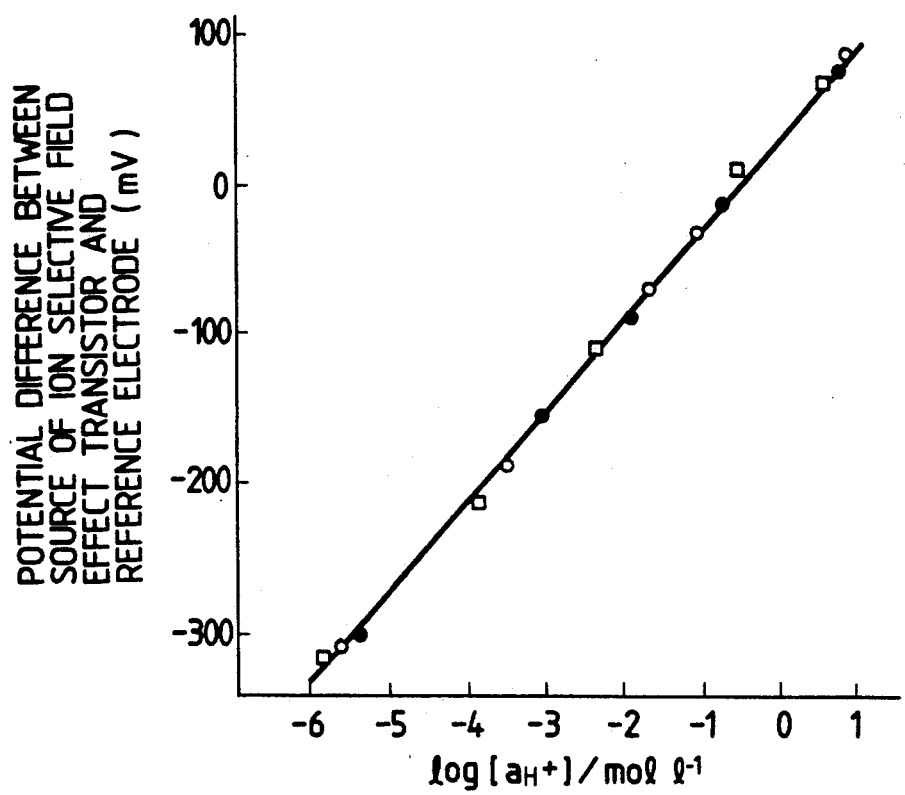
FIG. 2 is a graph showing the potential difference between the source of an ISFET having an ion sensing layer of tantalum nitride and an Ag/AgCl reference electrode of double-junction type compared to the concentration of hydrogen ions in aqueous acid solutions.

The ion-selective FET and a double-junction type Ag/AgCl reference electrode were both submerged in aqueous solutions of three different acids to determine the relationship between the hydrogen ion concentration in aqueous solution and the potential difference between the ISFET source and the reference electrode. The acids used were sulfuric acid, hydrochloric acid and nitric acid and their concentrations in solution were varied. The operating conditions of the ISFET for the measurement were as follows: drain-source voltage ($V_{DS}$)=2.50 V; drain current ($I_D$)=100 μA. The results are shown in FIG. 2 by ○, ● and □ for sulfuric acid, hydrochloric acid and nitric acid, respectively. From FIG. 2, it is shown that irrespective of acid type, the relationship of the potential difference between the FET source and the reference electrode compared to the logarithm of the hydrogen ion concentration is linear over a broad range of concentrations, and further that the measurement sensitivity (the change in voltage in response to a 10-fold change in concentration) is ca. 60 mV for each acid. Additionally, it took only about 5 seconds or less for the potential of the ion-selective FET of the present invention to become stable, thereby demonstrating its rapid response.

EXAMPLE 2

Figure 3:
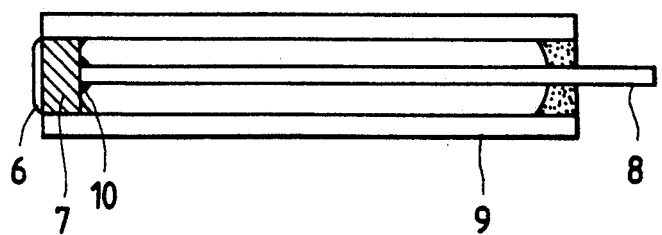
FIG. 3 is a longitudinal sectional view of a hydrogen ion electrode having an ion sensing layer 6 formed on the metal surface at the tip of the electrode, a titanium disk 7, a lead wire 8, a polycarbonate tube 9 and a soldering part 10.

Under the same conditions as in Example 1, a thin film of tantalum nitride (TaN) was formed on the surface of an electrode tip shown in FIG. 3, thereby fabricating a hydrogen ion electrode using the thin TaN film as an ion sensing layer. FIG. 3 illustrates the tantalum nitride (TaN) thin film 6, a titanium disk 7, a lead wire 8, a polycarbonate tube 9, and a soldering part 10.

The hydrogen ion electrode and a double-junction type Ag/AgCl reference electrode were both submerged in aqueous solutions of three different acids to determine the relationship between the concentration of hydrogen ions in aqueous solution and the potential difference between the hydrogen ion electrode and the reference electrode. The acids used were sulfuric acid, hydrochloric acid and nitric acid in various concentrations in solution. It was found that irrespective of acid type, the relationship of the potential difference between the hydrogen ion electrode and the reference electrode compared to the logarithm of the hydrogen ion concentration was linear over a broad concentration range, and further that the measurement sensitivity (the voltage change in response to a 10-fold change in concentration) is ca. 60 mV for each acid. Additionally, it took only about 15 seconds or less for the potential of the hydrogen ion electrode to become stable, thereby demonstrating its rapid response.

EXAMPLE 3

Figure 4:
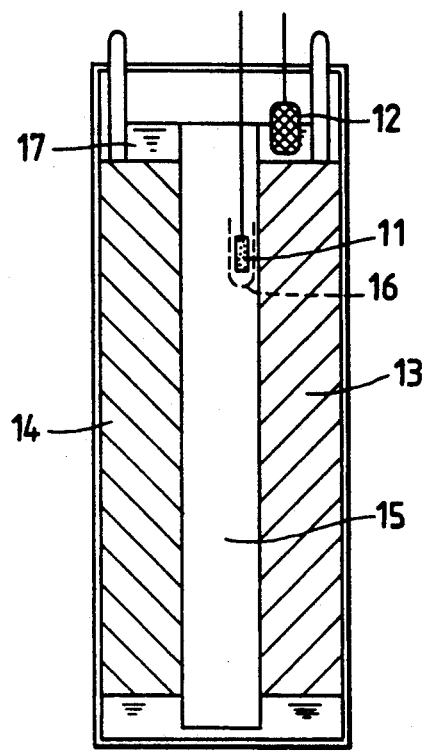
FIG. 4 is a sectional view of an automotive lead-acid battery having a couple of an ion-selective FET 11 and an Ag/AgCl reference electrode 12 submerged in the electrolyte 17, having a positive plate 13, a negative plate 14, a separator 15, an insulator membrane 16 for preventing contact between the ion-selective FET and the positive plate, and electrolyte 17.

The ion-selective FET fabricated in Example 1 and an Ag/AgCl reference electrode were both submerged in the electrolyte of an automotive lead-acid battery, and the potential difference between the ISFET and the reference electrode was measured at various stages of the transition from a fully charged to a fully discharged state. FIG. 4 shows how the ISFET and the reference electrode are installed in the lead-acid battery having the ion-selective FET 11, the reference electrode 12, a positive plate 13, a negative plate 14, a separator 15, an insulator membrane 16 for preventing contact between the ISFET and the positive plate, and the electrolyte 17. The operating conditions of the ISFET for the measurement were the same as those in Example 1. Similarly, the specific gravity of the electrolyte was measured with a float-type hydrometer.

Figure 5:
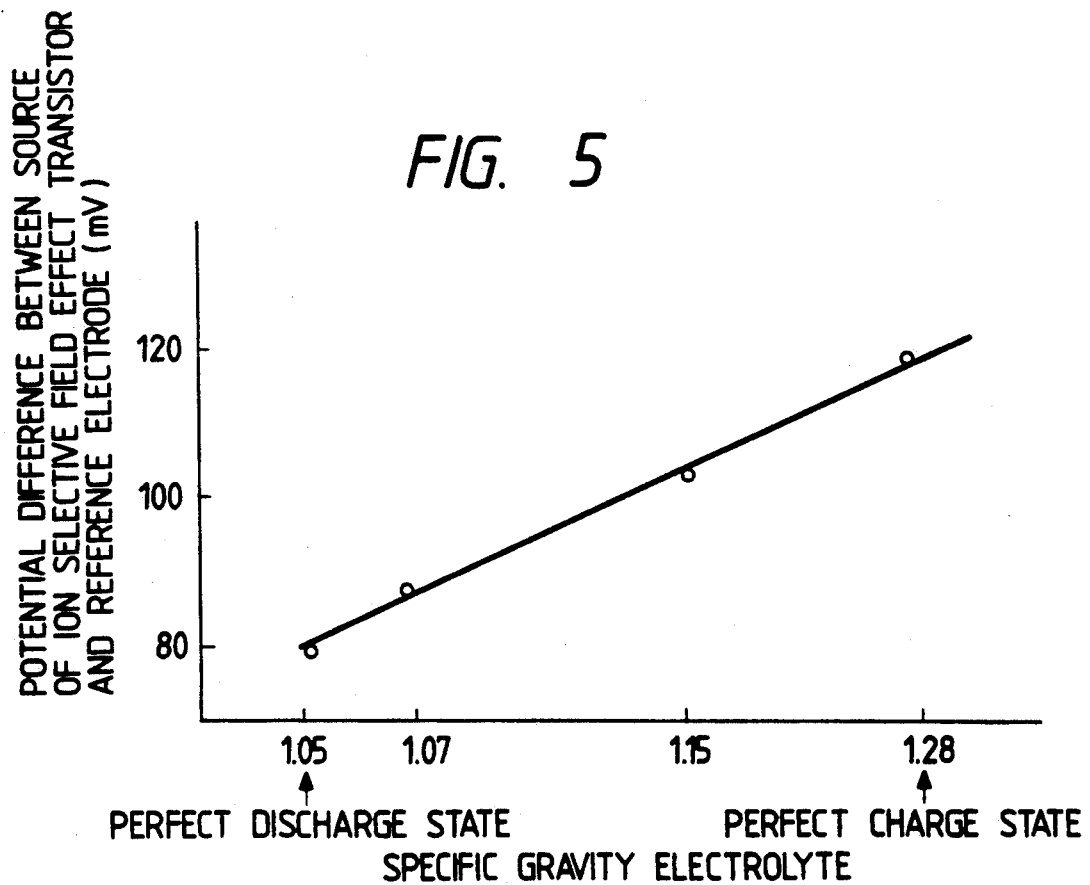
FIG. 5 is a graph showing the potential difference between the source of an ion-selective FET and a reference electrode compared to the specific gravity of sulfuric acid as an electrolyte in a lead-acid battery.

FIG. 5 shows the relationship of the potential difference between the ISFET source and the reference electrode as compared to the specific gravity of the electrolyte. When the specific gravity of the electrolyte was 1.28 (at full charge), the voltage between the ISFET source and the reference electrode was ca. 120 mV. In contrast, when the specific gravity of the electrolyte was 1.05 (at full discharge), the voltage of interest was ca. 80 mV. Over the concentration range defined by these two points, the potential difference between the ISFET source and the reference electrode as compared to the logarithm of the sulfuric acid activity was linear. As shown in FIG. 5, the specific gravity of the electrolyte can be determined by measuring the potential difference between the ion-selective FET and the reference electrode. Since it is known that the specific gravity of the electrolyte in lead-acid batteries is a direct indicator of their charge-to-discharge state, a specific stage of the transition from a charged to a discharged state or vice versa can be estimated by measuring the potential difference between the source of the ion-selective FET and the reference electrode.

EXAMPLE 4

A thin film of niobium pentoxide ($Nb_2O_5$) was formed on the gate insulator layer of an FET measuring 0.5×6.5×0.23 mm by plasma-assisted chemical vapor deposition (CVD). The thus-formed thin film served as an ion sensing layer. The feed gas was composed of niobium pentachloride ($NbCl_5$) and carbon dioxide ($CO_2$), and hydrogen ($H_2$) was used as a carrier gas. The substrate temperature was adjusted to 800° C. and an RF plasma was generated at 13.56 MHz. Niobium pentoxide was produced according to the following reaction scheme:

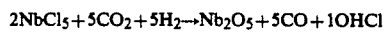

$$2NbCl_5 + 5CO_2 + 5H_2 \rightarrow Nb_2O_5 + 5CO + 10HCl$$

The thus-formed thin niobium pentoxide film had a thickness of ca. 2000 Å. The fabricated ion-selective FET had the same construction as that shown in FIG. 1.

EXAMPLE 5

A thin film of niobium nitride (NbN) was formed on the gate insulator layer of an FET measuring 0.5×6.5×0.23 mm by plasma-assisted CVD. The thus-formed thin film served as an ion sensing layer. The feed gas was composed of niobium pentachloride ($NbCl_5$) and nitrogen ($N_2$), and hydrogen was used as a carrier gas. The substrate temperature was adjusted to 700° C. and an RF plasma was generated at 13.56 MHz. Niobium nitride was produced according to the following reaction scheme:

$$2NbCl_5 + N_2 + 5H_2 \rightarrow 2NbN + 10HCl$$

The thus-formed thin niobium nitride film had a thickness of ca. 2000 Å. The fabricated ion-selective FET had the same construction as that shown in FIG. 1.

EXAMPLE 6

A thin film of zirconium nitride (ZrN) was formed on the gate insulator layer of an FET measuring $0.5 \times 6.5 \times 0.23$ mm, by plasma-assisted CVD. The thus-formed thin film served as an ion sensing layer. The feed gas was composed of zirconium tetrachloride ($ZrCl_4$) and ammonia ($NH_3$). The substrate temperature was adjusted to 600° C. and an RF plasma was generated at 13.56 MHz. Zirconium nitride was produced according to the following reaction scheme:

$$ZrCl_4 + NH_3 \rightarrow ZrN + HCl$$

The thus-formed thin zirconium nitride film had a thickness of ca. 3000 Å. The fabricated ion-selective FET had the same construction as shown in FIG. 1.

The method of providing the various ion sensing layers is in no way limited to those described in Examples 1-6, and various other methods can be adopted. For instance, the thin film of tantalum nitride may be formed by nitriding metallic tantalum in a hot nitrogen or ammonia atmosphere, the thin film of niobium pentoxide may be formed by oxidizing metallic niobium in a hot oxygen atmosphere, the thin film of niobium nitride may be formed by nitriding metallic niobium in a hot nitrogen or ammonia atmosphere, or the thin film of zirconium nitride may be formed by nitriding metallic zirconium in a hot nitrogen or ammonia atmosphere.

Further, the composition of the ion sensing layer is not limited to the stoichiometric compounds described in Examples 1-6, and other stoichiometric compounds may also be used. For example, ditantalum mononitride ($Ta_2N$) may be used as tantalum nitride, niobium monoxide (NbO), diniobium trioxide ($Nb_2O_3$) and niobium dioxide ($NbO_2$) may be used as niobium oxide, or diniobium mononitride ($Nb_2N$) may be used as niobium nitride. Needless to say, similar effects to those obtained in Examples 1-6 can be attained by using these alternative compounds.

As described above, the hydrogen ion concentration sensing device that is fabricated according to the invention by combining a reference electrode with an ISFET that has a thin film of a tantalum nitride, a niobium nitride, a zirconium nitride or a niobium oxide formed as an ion sensing layer on the surface of the gate insulator layer or the metallic surface, can indicate a broad range of hydrogen ion concentrations in terms of potential difference. Additionally, the device is easily handled, has a fast response speed and is adaptable for continuous measurement with the device being submerged in an aqueous solution of interest.

As a further advantage, each of the ion sensing materials used in the present invention, i.e., tantalum nitride, niobium nitride, zirconium nitride and niobium oxide, has very high chemical stability, so that the sensing device of the present invention can be used in aqueous solutions of various acids for a prolonged period and yet have very high reliability. Furthermore, the potential characteristics of the device are independent of the size of the ion sensing layer, so the device scale can be made very small by employing the most appropriate fabrication process.

Therefore, the hydrogen ion sensing device of the present invention is not only effective for measuring the lower concentration of hydrogen ions which has heretofore been measured with a glass electrode, but the device may also be installed in a lead-acid battery for keeping track of the transition of the battery from a charge to a discharge state or vice versa. Because of these advantages, the device is extremely industrially beneficial.

While certain preferred embodiments have been shown and described above, many changes and modifications within the spirit of the invention will be apparent to those of working skill in this technical field. Thus, the scope of the invention should be considered as limited only by the appended claims.

What is claimed is:

1. A device for measuring hydrogen ion concentration in an aqueous solution, comprising:
   means for sensing hydrogen ion concentration, said sensing means having an ion-sensitive layer coming in contact with said aqueous solution; and
   a reference electrode opposed to said sensing means, said ion-sensitive layer consisting of a member selected from niobium nitride and zirconium nitride.

2. A device according to claim 1, wherein said sensing means comprises an ion-sensitive field-effect transistor having said ion-sensitive layer formed on an insulated gate portion of said field-effect transistor.

3. A device according to claim 1, wherein said sensing means comprises a hydrogen ion electrode composed of a double layer of a metallic substrate and said ion-sensitive layer.

4. A device according to claim 1, wherein the thin film formed on said sensing means is composed of niobium nitride.

5. A device according to claim 1, wherein the thin film formed on said sensing means is composed of zirconium nitride.

6. A device according to claim 1, said device being integrally built into and adapted for use with a lead-acid battery including a housing, a positive plate contained in said housing, a negative plate opposite said positive plate, a separator interposed between said positive plate and said negative plate, an insulator membrane for preventing contact between said sensing means having said thin film thereon and said positive plate, and said aqueous solution, said aqueous solution comprising an electrolyte, and wherein said positive plate, said negative plate and said sensing means are at least partially immersed in said electrolyte.

7. A device according to claim 2, said device being integrally built into and adapted for use with a lead-acid battery including a housing, a positive plate contained in said housing, a negative plate opposite said positive plate, a separator interposed between said positive plate and said negative plate, an insulator membrane for preventing contact between said sensing means having said thin film thereon and said positive plate, and said aqueous solution, said aqueous solution comprising an electrolyte, and wherein said positive plate, said negative plate and said sensing means are at least partially immersed in said electrolyte.

8. A device according to claim 3, said device being integrally built into and adapted for use with a lead-acid battery including a housing, a positive plate contained in said housing, a negative plate opposite said positive plate, a separator interposed between said positive plate and said negative plate, an insulator membrane for preventing contact between said sensing means having said thin film thereon and said positive plate, and said aqueous solution, said aqueous solution comprising an electrolyte, and wherein said positive plate, said negative plate and said sensing means are at least partially immersed in said electrolyte.

9. A device for measuring hydrogen ion concentration in an aqueous solution, comprising:
means for sensing hydrogen ion concentration, said sensing means having an ion-sensitive layer coming in contact with said aqueous solution; and
a reference electrode opposed to said sensing means, said ion-sensitive layer consisting of tantalum nitride;
said device being integrally built into and adapted for use with a lead-acid battery including a housing, a positive plate contained in said housing, a negative plate opposite said positive plate, a separator interposed between said positive plate and said negative plate, an insulator membrane for preventing contact between said sensing means having said ion-sensitive layer thereon and said positive plate, and said aqueous solution, said aqueous solution comprising an electrolyte, and wherein aid positive plate, said negative plate and said sensing means are at least partially immersed in said electrolyte.

10. A device for measuring hydrogen ion concentration in an aqueous solution, comprising:
means for sensing hydrogen ion concentration, said sensing means having an ion-sensitive layer coming in contact with said aqueous solution; and
a reference electrode opposed to said sensing means, said ion-sensitive layer consisting of niobium oxide;
said device being integrally built into and adapted for use with a lead-acid battery including a housing, a positive plate contained in said housing, a negative plate opposite said positive plate, a separator interposed between said positive plate and said negative plate, an insulator membrane for preventing contact between said sensing means having said ion-sensitive layer thereon and said positive plate, and said aqueous solution, said aqueous solution comprising an electrolyte, and wherein aid positive plate, said negative plate and said sensing means are at least partially immersed in said electrolyte.

11. A device according to claim 4, said device being integrally built into and adapted for use with a lead-acid battery including a housing, a positive plate contained in said housing, a negative plate opposite said positive plate, a separator interposed between said positive plate and said negative plate, an insulator membrane for preventing contact between said sensing means having said thin film thereon and said positive plate, and said aqueous solution, said aqueous solution comprising an electrolyte, and wherein said positive plate, said negative plate and said sensing means are at least partially immersed in said electrolyte.

12. A device according to claim 5, said device being integrally built into and adapted for use with a lead-acid battery including a housing, a positive plate contained in said housing, a negative plate opposite said positive plate, a separator interposed between said positive plate and said negative plate, an insulator membrane for preventing contact between said sensing means having said thin film thereon and said positive plate, and said aqueous solution, said aqueous solution comprising an electrolyte, and wherein said positive plate, said negative plate and said sensing means are at least partially immersed in said electrolyte.

13. A device according to claim 1, wherein said reference electrode comprises a double-junction-type Ag/AgCl electrode.

14. A device for measuring hydrogen ion concentration in an aqueous solution, comprising:
means for sensing hydrogen ion concentration, said sensing means having an ion-sensitive layer coming in contact with said aqueous solution; and
a reference electrode opposed to said sensing means, said ion-sensitive layer consisting of a member selected form niobium nitride and zirconium nitride;
wherein said sensing means comprises an ion-sensitive field-effect transistor having said ion-sensitive layer formed on an insulated gate portion of said field-effect transistor; and
wherein said hydrogen ion electrode has a wire-like shape and has a cross-sectional area of approximately $0.23 \times 0.5$ mm.

15. A device for measuring hydrogen ion concentration in an aqueous solution, comprising:
means for sensing hydrogen ion concentration, said sensing means having an ion-sensitive layer coming in contact with said aqueous solution; and
a reference electrode opposed to said sensing means, said ion-sensitive layer consisting of a member selected form niobium nitride and zirconium nitride;
wherein said sensing means comprises a hydrogen ion electrode composed of a double layer of a metallic substrate and said ion-sensitive layer; and
wherein said hydrogen ion electrode includes a polycarbonate tube.

16. A device according to claim 2, wherein said hydrogen ion electrode and said reference electrode are built integrally into a field-effect transistor.

17. A device according to claim 6, wherein said lead-acid battery includes first and second electrodes having a space therebetween, said sensing means being positioned in said space between said first and second electrodes.

18. A device according to claim 3, wherein said field-effect transistor and said reference electrode are submerged in an aqueous solution of an acid, said acid comprising one of sulfuric acid, hydrochloric acid, and nitric acid.

19. A device for measuring hydrogen ion concentration in an aqueous solution, comprising:
means for sensing hydrogen ion concentration, said sensing means having an ion-sensitive layer coming in contact with said aqueous solution; and
a reference electrode opposed to said sensing means, said ion-sensitive layer consisting of a member selected form niobium nitride and zirconium nitride;
wherein said sensing means comprises a hydrogen ion electrode composed of a double layer of a metallic substrate and said ion-sensitive layer; and wherein a voltage relationship between said hydrogen ion electrode and the reference electrode compared to a logarithm of a hydrogen ion concentration of said aqueous solution is linear over a predetermined range of concentration of hydrogen ions in said aqueous solution.

20. A device for measuring hydrogen ion concentration in an aqueous solution, comprising:

means for sensing hydrogen ion concentration, said sensing means having an ion-sensitive layer coming in contact with said aqueous solution; and a reference electrode opposed to said sensing means, said ion-sensitive layer consisting of a member selected form niobium nitride and zirconium nitride;

wherein said sensing means comprises an ion-sensitive field-effect transistor having said ion-sensitive layer formed on an insulated gate portion of said field-effect transistor;

wherein said field-effect transistor includes a source electrode, and wherein a relationship of the voltage between said source electrode and the reference electrode compared to a logarithm of a hydrogen ion concentration of said aqueous solution is linear over a predetermined range of concentration of hydrogen ions in said aqueous solution.

* * * * *